United States Patent
Hashimoto

(10) Patent No.: US 8,487,286 B2
(45) Date of Patent: Jul. 16, 2013

(54) RADIATION THERAPY EQUIPMENT

(75) Inventor: Teruo Hashimoto, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 292 days.

(21) Appl. No.: 12/862,089

(22) Filed: Aug. 24, 2010

(65) Prior Publication Data

US 2011/0049395 A1 Mar. 3, 2011

(30) Foreign Application Priority Data

Aug. 25, 2009 (JP) ................ P2009-194829

(51) Int. Cl.
*G21K 5/04* (2006.01)

(52) U.S. Cl.
USPC ............ 250/505.1; 250/515.1; 250/517.1; 250/519.1; 378/145

(58) Field of Classification Search
USPC ......... 250/492.1, 492.3, 505.1, 515.1, 517.1; 378/145, 147, 148, 149, 150, 151, 152, 153
See application file for complete search history.

(56) References Cited

U.S. PATENT DOCUMENTS

| 4,794,629 | A | * | 12/1988 | Pastyr et al. | ........... | 378/152 |
| 6,711,237 | B1 | * | 3/2004 | Schlegel et al. | ........... | 378/152 |
| 2005/0063516 | A1 | * | 3/2005 | Kato et al. | ........... | 378/152 |
| 2006/0067481 | A1 | * | 3/2006 | Morton | ........... | 378/151 |
| 2008/0205599 | A1 | * | 8/2008 | Hashimoto | ........... | 378/148 |

FOREIGN PATENT DOCUMENTS

JP 2002-253686 9/2002

* cited by examiner

*Primary Examiner* — Nicole Ippolito
(74) *Attorney, Agent, or Firm* — Oblon, Spivak, McClelland, Maier & Neustadt, L.L.P.

(57) ABSTRACT

Radiation therapy equipment includes a multi-divided irradiation collimator leaf plates for setting irradiation field as approximately close to a target region as possible by avoiding backlashes due to a plurality of gears for driving a plurality of leaf plates. The plurality of leaf plates is respectively connected to a plurality of constant force springs that are coaxially supported by a pair of rotation shafts so as to be constantly forced in a closing direction. Each leaf plate is moved in an opening direction by rolling up a wire connected to the leaf plate.

13 Claims, 12 Drawing Sheets

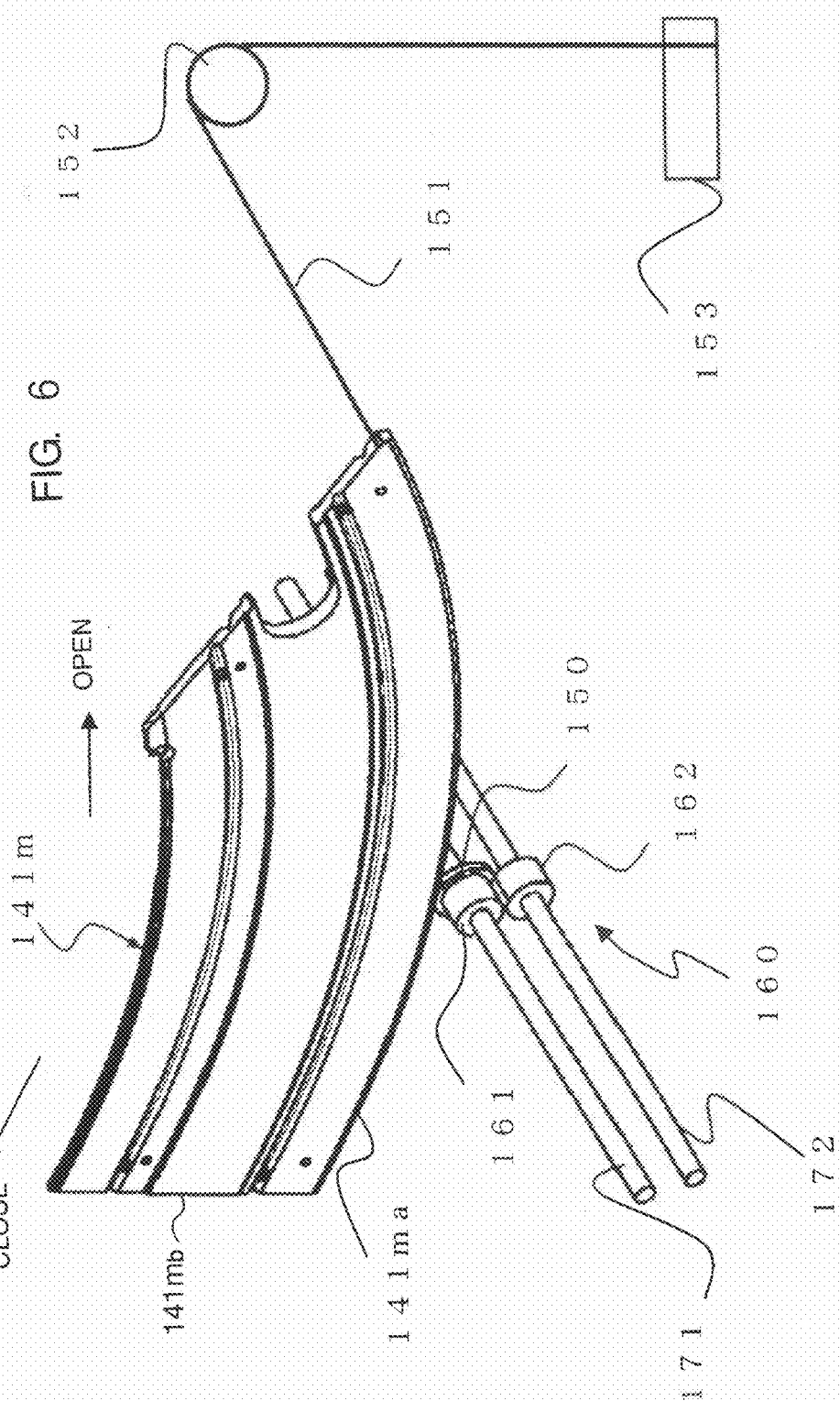

RADIATION THERAPY EQUIPMENT

CROSS-REFERENCE TO RELATED APPLICATIONS

This application is based upon and claims the benefit of priority from Japanese Patent Application No. 2009-194829, filed on Aug. 25, 2009, the entire contents of which are expressly incorporated herein by reference.

BACKGROUND

A. Field

Embodiments described herein relate generally to radiation therapy equipment having a multi-divided irradiation collimator that can accurately determine an irradiation field of radiation as similar to a configuration of a desired region on an object.

B. Background

Typically, the radiation therapy equipment has an irradiation head unit for irradiating radiation on an object. In the irradiation head unit, an irradiation collimator (i.e., radiation collimator) is installed to determine an irradiation field on a desired treatment target region, such as a malignant tumor region of an object for preventing a radiation hazard from unnecessary radiation regions on the object. To reduce the radiation hazard as much as possible, it is required for the irradiation collimator to determine the irradiation field as accurately as possible to a configuration of the target treatment region. Usually, the irradiation collimator is comprised of an upper pair of collimator blocks provided at a near side of a radiation source along the radiation axis and a lower pair of collimator blocks provided at a lower position than the upper pair of collimator blocks along the radiation axis. The lower pair of collimator blocks is positioned so as to orthogonally cross the upper pair of collimator blocks.

The pair of upper collimator blocks is provided so as to face with each other with centering an irradiation axis of the radiation. The pair of upper collimator blocks is driven so as to approach or get away from each other along an arc shaped tracking direction (X-direction). The arc is a portion of a circle with centering the radiation source. The pair of lower collimator blocks is also provided so as to face with each other with centering an irradiation axis of the radiation. The pair of lower collimator blocks is driven so as to approach or get away from each other along an orthogonal arc shaped tracking direction (Y-direction) to the X-direction for tracking by the upper collimator blocks. Each of the lower collimator blocks is comprised of a multi-divided collimator block that is constructed by a plurality of closely attached leaf plates.

Each of the plurality of leaf plates has an arc shaped tracking surface facing the radiation irradiation axis and a toothed configuration of a screw is provided on the tracking surface in order to engage with a driving gear. The driving gear is fixed to a tip portion a rotation shaft. The shaft is rotated by a motor of a driving source through a driving power transmitting mechanism such as worm gears. A detection unit, such as a potentiometer or an encoder is provided to detect a driven amount of the gears. Based on the data detected by the detection unit, each of the leaf plates in the lower collimator blocks is independently driven to a desired position.

Thus, in a conventional radiation therapy equipment, an irradiation field is formed so as to be approximate to an irregular shape of a target treatment region by moving the pair of upper collimator blocks in the X direction and each of the plurality of leaf plates in each of the pair of lower collimator blocks in the Y direction being orthogonal to the X direction.

However, the conventional irradiation collimator needs to use the driving power transmitting mechanism to rotate a driving gear through a shaft by transmitting a driving power of a motor to independently move each of the plurality of leaf plates in the lower collimator block. Since the conventional driving power transmitting mechanism is constructed by combining various types of toothed wheels, backlash due to the respective toothed wheels are accumulated, it has difficult to accurately control to position each of the leaf plates in the irradiation collimator.

Further, in the conventional irradiation collimator, the driving power transmitting mechanism needs to be provided so as that the motor must be positioned in parallel or at a right angle to the rotation shaft for each of the leaf plates. Due to such a limitation, it has been difficult to increase the number of the shaft driving power transmitting mechanism to increase the number of the leaf plates in a limited space of the irradiation head unit.

Recently, to protect against radiation hazards, a requirement for setting an irradiation field as accurately close to a configuration of a target treatment region is strongly increased. To set the irradiation field as closely as possible to an irregular shape of the target treatment region, the number of the leaf plates in the lower collimator blocks needs to be increased with decreasing each thickness of the leaf plates. However, as mentioned above, it has been difficult to increase the number of the shaft driving power transmitting mechanisms to increase the number of the leaf plates in a limited space of the irradiation head unit.

SUMMARY

An embodiment of the present invention addresses these and other problems and drawbacks and provides an irradiation collimator installing in a radiation therapy equipment that can perform a high accuracy radiation therapy. While a number of the driving power transmission mechanisms are increased with increasing a number of the leaf plates, they can be freely installed in a limited space of the irradiation unit. According to an embodiment, a plurality of constant force springs with no change in torque regardless of a length of stroke are used for driving each of the plurality of leaf plates. The plurality of constant force springs are coaxially supported on a pair of rotation shafts. Each rotation shaft is fixed to each of a plurality of driving gears. Each of the driving gears is engaged to a toothed configuration provided on each tracking surface of the leaf plates. As a result, a constant force is applied to each of the leaf plates so as to move in a closing direction. While a constant force is applied to each of the leaf plates is constantly in a closing direction by the constant force spring, each of the leaf plates is moved in an opening direction by rewinding up a wire connected to each of plates through a pulley. By using a plurality of constant force springs, the conventional backlashes due to the usage of a plurality of driving gears can be substantially avoided and an accurate irradiation field can be precisely set up by increasing the number of the leaf plates. Further, an increased number of transmission mechanisms for moving each of the increased number of leaf plates also can be freely installed in a limited space of the irradiation unit.

An embodiment of the radiation therapy equipment includes a radiation collimator unit for shielding radiation from a radiation source so as to limit an irradiation field of the radiations onto a target treating region. The radiation collimator unit is comprised of a pair of movable collimator blocks, each block including a plurality of movable leaf plates, each leaf plate having a toothed configuration on an arc shaped tracking surface of the leaf plate, a plurality of driving gears configured to independently drive each of the plurality of leaf plates by engaging with the toothed configuration provided on each tracking surface of the plurality of leaf plates, a plurality of constant force spring units respectively coupled to each of the plurality of driving gears configured to constantly apply force to each of the plurality of driving gears so as to independently move each of the plurality of leaf plates in closing directions, a plurality of wires connected to each of the plurality of leaf plates, and a plurality of roll-up units configured to independently roll-up each of the plurality of wires so as to independently move each of the leaf plates in an opening direction against each of the closing forces of the plurality of constant force spring units.

Radiation therapy equipment according to the embodiment can safely protect an object even when the wire connected to the movable leaf plate is accidentally cut because the leaf plate immediately closes the irradiation aperture by the closing force due to the constant force spring unit.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 6 is an appearance diagram illustrating a leaf plate and a leaf driving mechanism used in the movable irradiation collimator according to an embodiment of the present invention.

DETAILED DESCRIPTION

Figure 1:
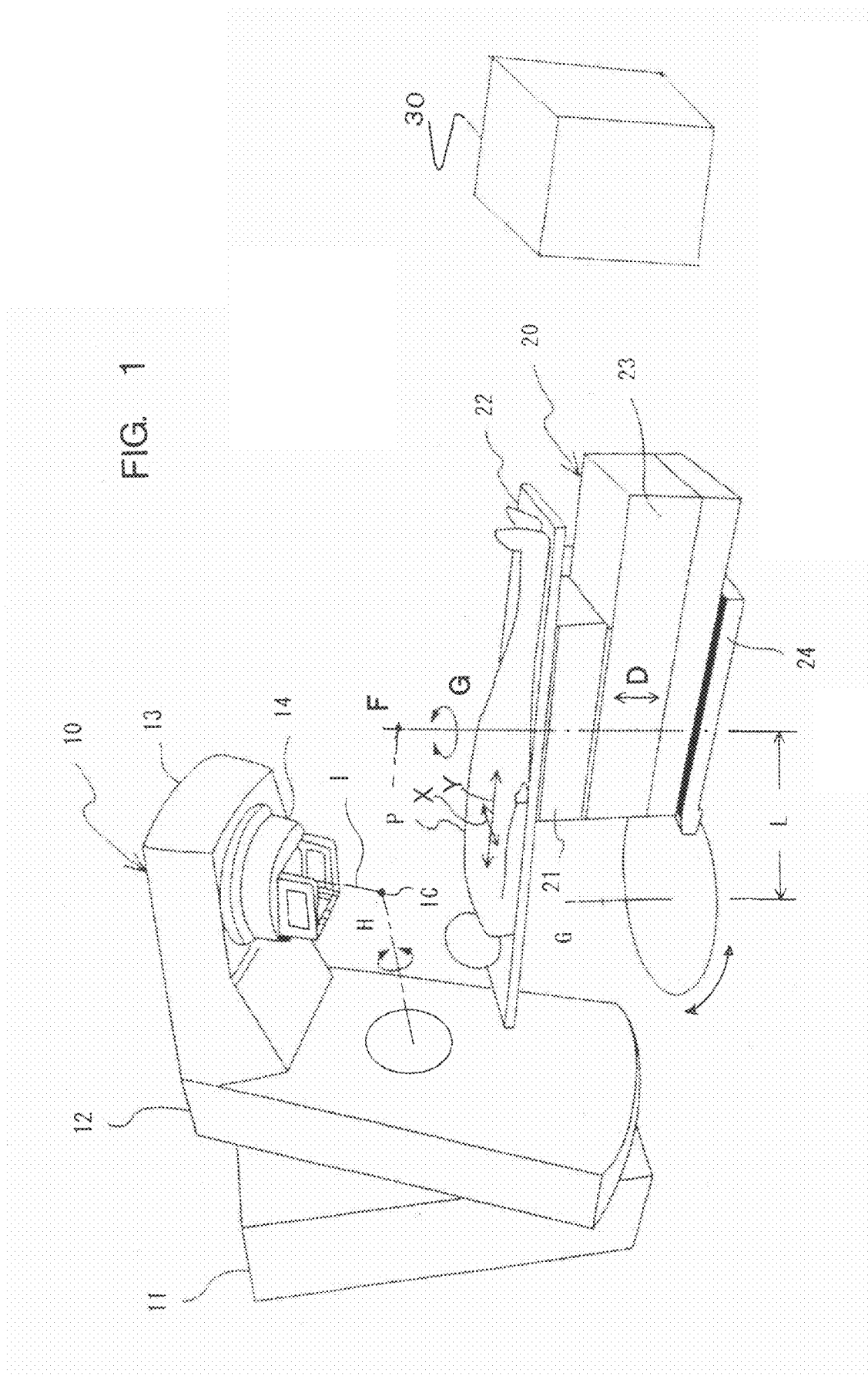
FIG. 1 is a block diagram illustrating an entire construction of radiation therapy equipment according to an embodiment of the present invention.

Reference will first be made to the entire construction of a radiation therapy equipment according to an exemplary embodiment of the present invention. FIG. 1 illustrates an entire construction of radiation therapy equipment according to this embodiment. Radiation therapy equipment 100 is comprised of a radiation irradiation section 10 for irradiating radiation emitted from a radiation source on an object P, a treatment table section 20 for positioning of an irradiation region by moving a top plate 22 supporting the object P, a control section 30 for totally controlling the radiation irradiation section 10 and the treatment table section 20.

The radiation irradiation section 10 includes a fixed gantry 11 provided on a floor of the radiation therapy room, a rotation gantry 12 provided on the fixed gantry 11 so as to rotate around a horizontal rotation axis H of the fixed gantry 11, an irradiation head unit 13 provided on a head portion of the movable gantry 12 for irradiating ray beams on an affected region of the object P, and a rotatable irradiation collimator 14 installed in the irradiation head unit 13. As shown in FIG. 1, the irradiation collimator 14 may rotate around an irradiation axis i of the irradiation head unit 13. The horizontal rotation axis H of the rotation gantry 12 crosses the irradiation axis I of the ray-beam irradiation head unit 13 at an iso-center IC. The rotation gantry 12 can be moved in correspondence to various irradiation manners, such as a rotation irradiation, a pendulum irradiation and an intermittent irradiation.

The treatment table section 20 can be rotated on the floor in an arrow direction G at a prescribed angle along an arc circle with centering the iso-center IC. The treatment table section 20 includes an upper mechanism 21 for supporting the top plate 22, a lifting mechanism 23 for lifting the upper mechanism 21, and a lower mechanism 24 for supporting the lifting mechanism 23. The lifting mechanism 23 moves up and down the upper mechanism 21 and the top plate 22 in an arrow D direction. The lower mechanism 24 rotates the lifting mechanism 23 around an axis passing the iso-center IC at a position F that has a distance L in a horizontal (D) direction from the IC axis. In addition to the rotation of the lifting mechanism 23, the upper mechanism 21 and the top plate 22 also rotate at a prescribed angle in the horizontal direction.

The control section 30 includes an operation unit (not shown). Through the operation unit, a medical staff sets up a position of the top plate 22 supporting an object P and an irradiation field determined by the irradiation collimator 14.

In the irradiation unit 13, an irradiation collimator 14 is installed so as to rotate around the irradiation axis I. The irradiation collimator 14 limits radiation so as to irradiate radiation just on a desired target treatment region, such as a malignant tumor, while avoiding unnecessary irradiation on normal tissues. The irradiation collimator 14 is made of a heavy metal, such as tungsten, for prohibiting radiation onto unnecessary regions, i.e., normal tissues.

Figure 2:
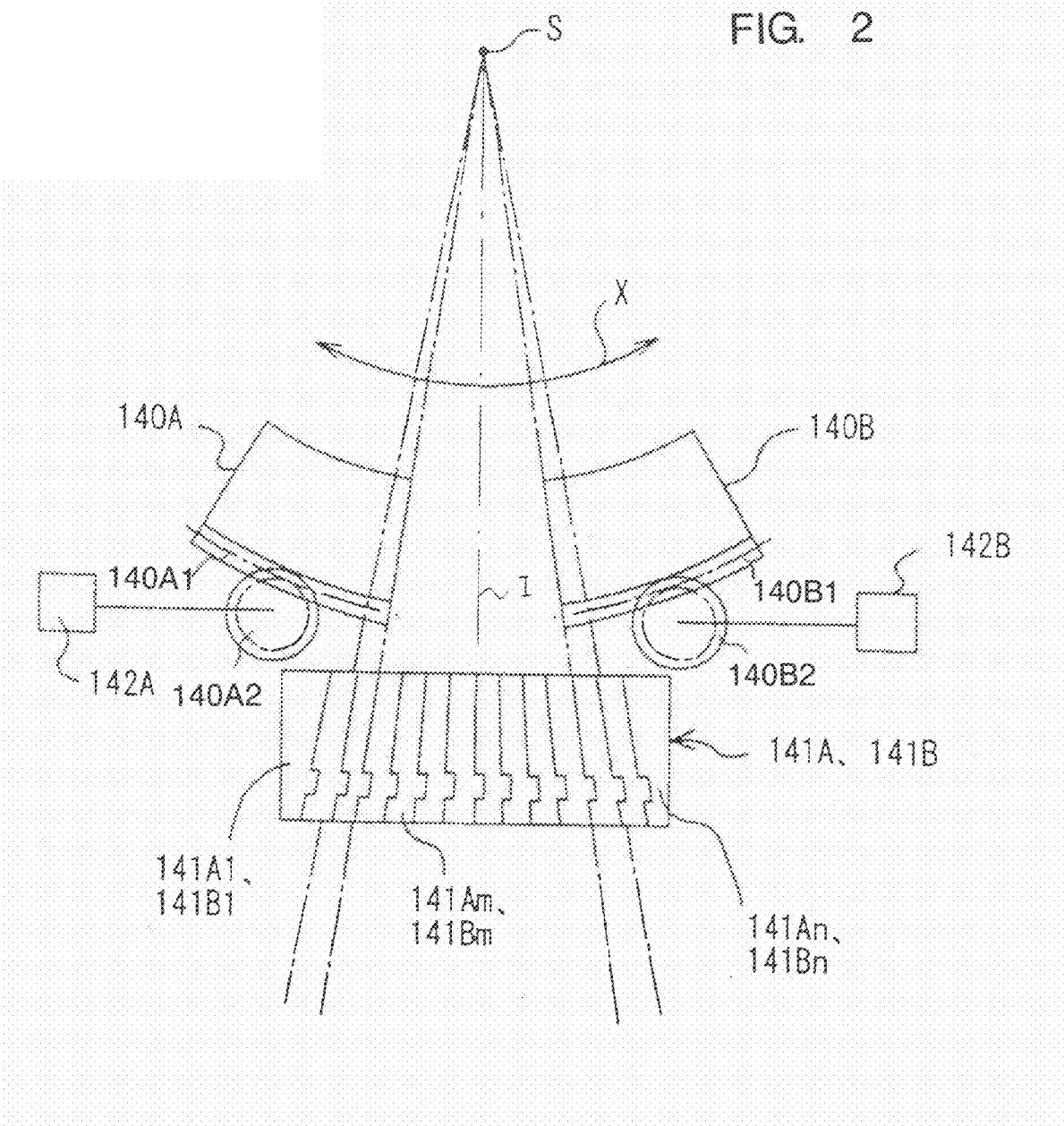
FIG. 2 is a sectional view illustrating the construction of a movable irradiation collimator according to an embodiment of the present invention.

FIG. 2 is a cross-sectional view of the irradiation collimator 14 along Y axis direction. As illustrated in figure, the irradiation collimator 14 is comprised of a pair of upper collimator blocks 140A and 140B facing the irradiation axis I and a pair of lower collimator blocks 141A and 141B. The pair of upper collimator blocks 140A and 140B is positioned at a radiation source S side. The pair of lower collimator blocks 141A and 141B is provided under the pair of upper collimator blocks 140A and 140B and arranged so as to be orthogonal to the arranged direction of the upper collimator blocks.

Toothed configurations 140A1 and 140B1 are respectively provided on each under surface of the upper collimator blocks 140A and 140B so as to engage to a pair of driving gears 140A2 and 140B2. A pair of driving units 142A and 142B drives the pair of driving gears 140A2 and 140B2 to approach or move apart the pair of upper collimator blocks 140A and 140B in the arrow X direction along an arc shaped tracking surface with each other. A pair of lower collimator blocks 141A and 141B is provided under the pair of upper collimator blocks 140A and 140B so as to face the irradiation axis I with each other. The lower collimator blocks 141A and 141B are constructed by a plurality of leaf plates 141Am (m=1~n) and 141Bm (m=1~n), respectively.

Figure 3:
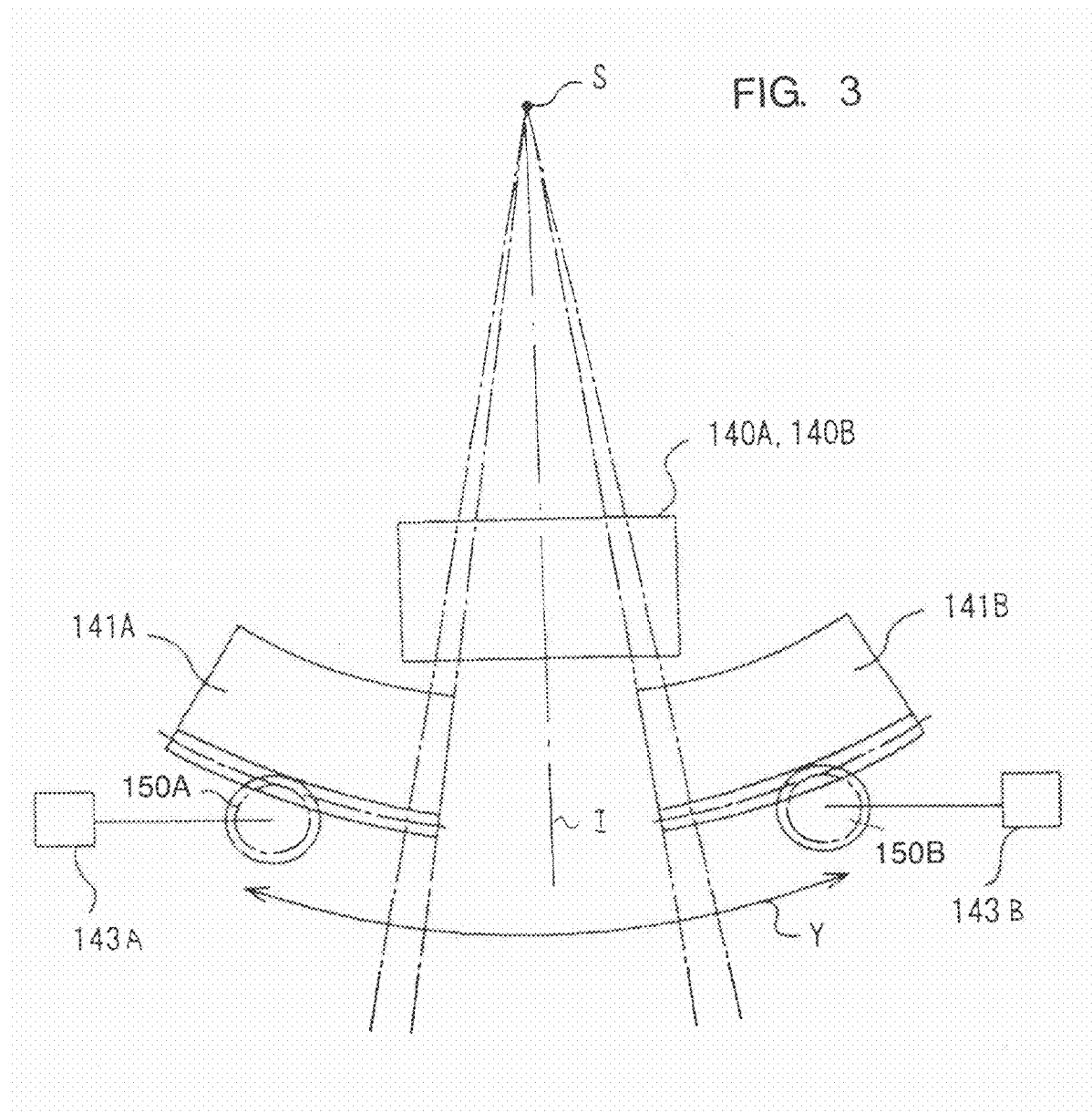
FIG. 3 is an orthogonal section view of the movable irradiation collimator illustrated in FIG. 2.

FIG. 3 is a side view of the irradiation collimator 14 viewing an orthogonal direction of FIG. 2. The pair of lower collimator blocks 141A and 141B is orthogonally provided under the pair of upper collimator blocks 140A and 140B facing the irradiation axis I with each other. Toothed configurations are respectively provided on each under surface of the lower collimator blocks 141A and 141B so as to engage to a pair of driving gears 150A and 150B. A pair of driving units 143A and 143B drives the pair of driving gears 150A and 150B to approach or move apart the pair of lower collimator blocks 141A and 141B in the arrow Y direction along an arc shaped tracking surface with each other. As illustrated in FIG. 2, each of the pair of lower collimator blocks 141A and 141B is a multi-divided collimator block that is comprised of a plurality of leaf plates. Thus, the collimator block 141A is constructed by closely adjoining a plurality of leaf plates 141 Am (m=1~n). And the collimator block 141B is constructed by closely adjoining a plurality of leaf plates 141Bm (m=1~n).

Figure 4:
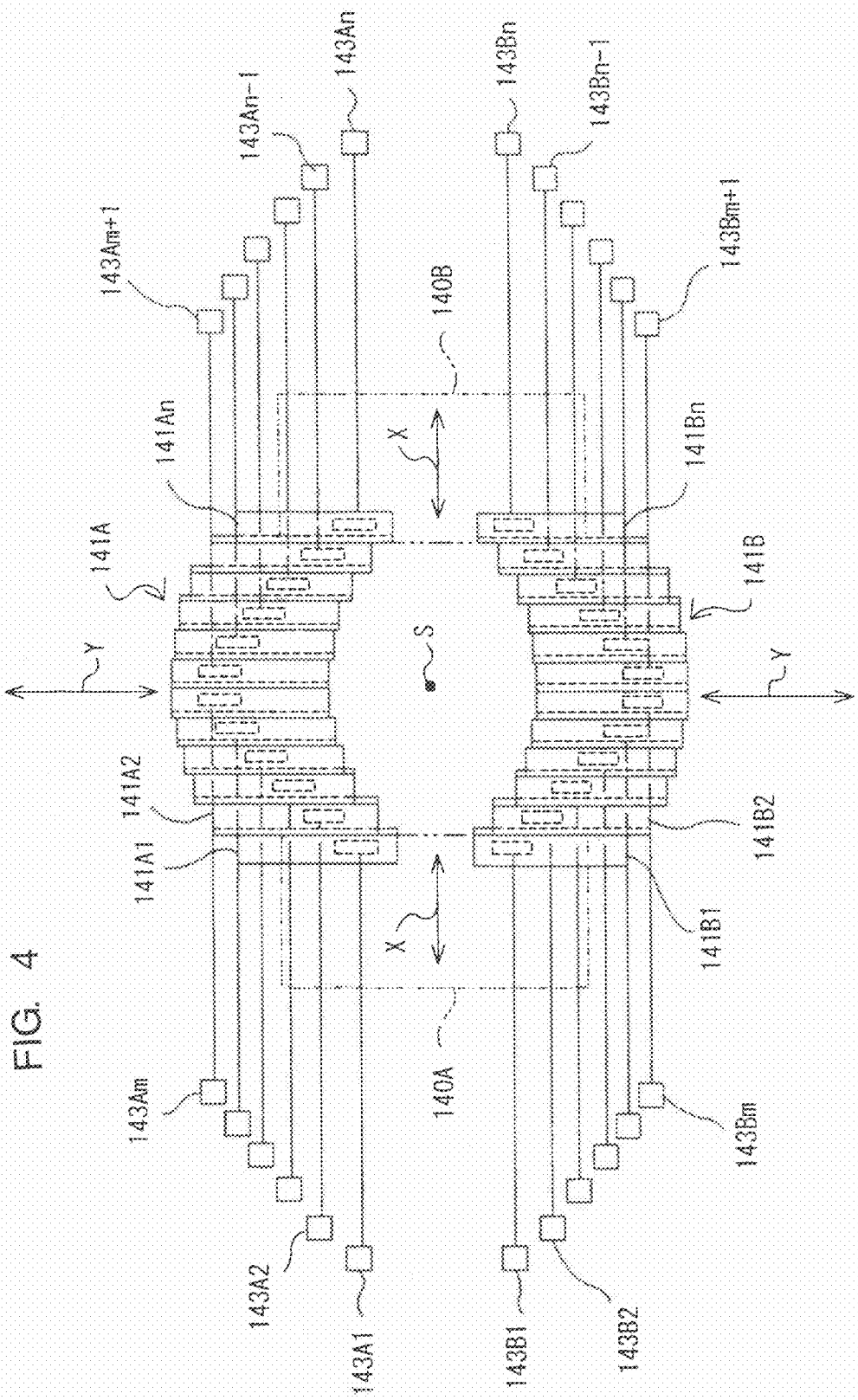
FIG. 4 is a plain view of the movable irradiation collimator illustrated in FIGS. 2 and 3 for determining an irradiation field.

FIG. 4 is a plane view of the pair of multi-divided irradiation collimator blocks. Toothed configurations are provided on each tracking surface of the leaf plates constructing the lower collimator blocks 141A and 141B. The toothed configurations on each of the leaf plates are respectively engaged to a plurality of driving gears. Each of the driving gears is respectively driven by a plurality of drive units 143A1 through 143An, and 143B1 through 143Bn so as to respectively move the plurality of leaf plates 141A1 through 141An and 141B1 through 141Bn in desired positions.

Figure 5:
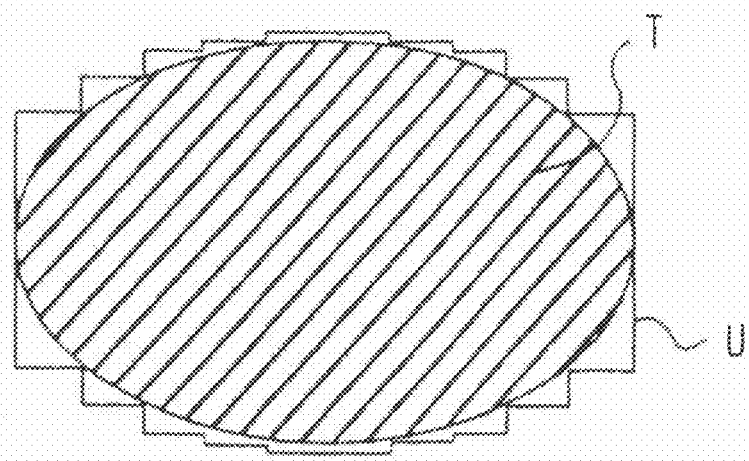
FIG. 5 is an explanatory plain view of the irradiation field formed by the movable irradiation collimator illustrated in FIG. 4.

Thus, the irradiation collimator 14 moves the pair of upper collimator blocks 140A and 140B so as to approach to or secede from each other in the X direction passing through a center axis of the radiation source S. Further the irradiation collimator 14 moves each of the leaf plates 141A1 through 141An and 141B1 through 141Bn in the pair of lower multi-divided irradiation collimator blocks 141A and 141B so as to approach to or move away from each other in the Y direction passing through a center axis of the radiation source S. By moving both upper collimator blocks 140A and 140B and each of the leaf plates in the lower multi-divided irradiation collimator blocks, a desired irradiation field U (FIG. 5) is formed. FIG. 5 depicts the irradiation field U formed on an irregular shape T of a target treatment region so as closely as possible by the irradiation collimator 14.

To make the shape of the irradiation field U approximate to the irregular shape T of the target treatment region, it is required to accurately move each of the leaf plates 141A1 through 141An and 141B1 through 141Bn in the lower collimator blocks, independently, so as to coincide with the irregular shape T. To accurately move each of the leaf plates 141A1 through 141An and 141B1 through 141Bn, back-lashes need to be avoided due to the driving mechanism including each of the driving gears that respectively engage with each toothed configuration formed on an arc surface of the leaf plate and each position of the leaf plate needs to be accurately detected.

FIG. 6 illustrates the driving mechanism according to the present embodiment for driving a leaf plate 141m (m=1~n) of the multi-divided irradiation collimator block. A left-side edge surface 141mb of the leaf plate 141m constructs an edge surface of the irradiation field as illustrated in FIG. 4. Thus, when the left-side edge surface 141mb of the leaf plate 141m is moved in the left direction of the drawing and a right-side edge surface of an opposite side leaf plate (not shown) facing the leaf plate 141m moves the right direction, an irradiation field formed by the pair of collimator leaf plates 141m is closed. On the contrary, each of the pair of leaf plates 141m moves in an opposite direction with each other, the irradiation field is widely opened.

As illustrated in FIG. 6, each of the leaf plates 141m has an arc shaped tracking surface, and toothed configurations (not shown) are formed on an outer side surface 141ma of the leaf plates 141m. A driving gear 150 is engaged with the toothed configurations provided the outer side surface 141ma. The driving gear 150 is coaxially fixed to either one drum 161 of the constant force spring 160 for constantly tensioning the leaf plate 141m in a closing direction through the driving gear 150.

Figure 7B:
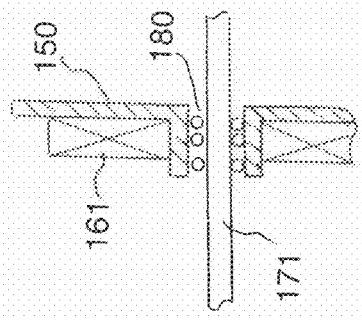
FIG. 7B is a cross-sectional view of the driving mechanism along A-A line shown in FIG. 7A.
Figure 7A:
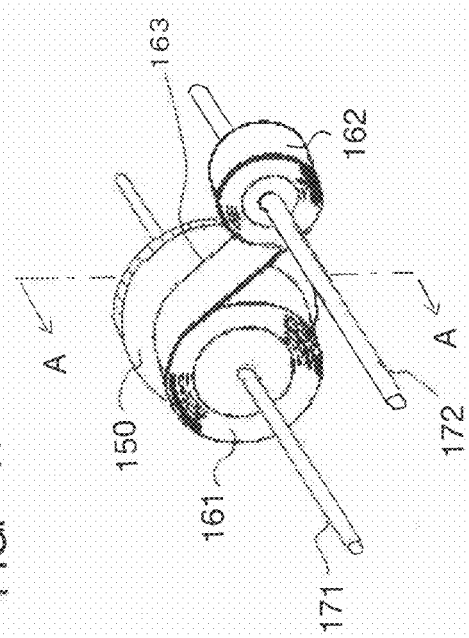
FIG. 7A is an enlarged view of the driving mechanism including the constant force spring shown in FIG. 6.
Figure 8:
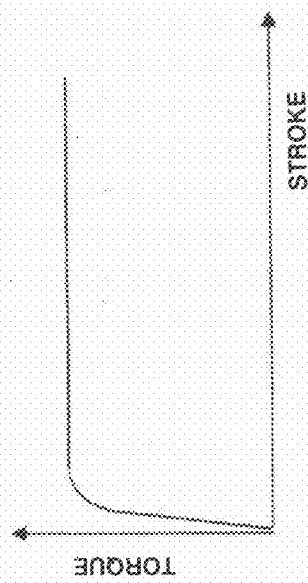
FIG. 8 is a characteristic curve of the constant force spring.

FIG. 7A illustrates a construction of the constant force spring 160 for constantly tensioning the driving gear 150. The constant force spring 160 has a characteristic feature that a constant torque (output power) is kept regardless the stroke (number of turns). As illustrated in FIG. 7A, the constant force spring 160 rolls up a belt-like spring 163 on a first drum 161 and also reversely rolls up the belt-like spring 163 on a second drum 162. When the belt-like spring 163 is rolled up on the second drum 162, a constant rotation torque toward the first drum 161 is tensioned regardless the rolled up length (stroke) of the belt-like spring 163. FIG. 8 shows the characteristic features of the constant force spring. Wherein, the horizontal axis shows the stroke of the roll upspring 163, and the vertical axis shows the rotation torque. In a central hollow portion of the drum 161 of the constant force spring 160, a first shaft 171 is rotatably inserted. Similarly, a second shaft 172 is rotatably inserted into a central hollow portion of the second drum 162 of the constant force spring 160. The second rotation shaft 172 is provided in parallel to the first rotation shaft 171. The first rotation shaft 171 is fixed to the driving gear 150.

FIG. 7B is a cross-sectional view of the first drum of the constant force spring along A-A direction shown in FIG. 7A. As illustrated in FIG. 7B, the first drum 161 of the constant force spring is constructed by rolling up a belt-like spring. One edge portion of the belt-like spring is coaxially fixed to a hollow portion of the driving gear 150. A first shaft 171 is inserted through a central hollow portion of the first drum 161 and rotatably supported through bearings 180. Similarly, a second shaft 172 is rotatably inserted into a central hollow portion of the second drum 162 of the constant force spring 160. Thus, one constant force spring 160 is supported by a pair of rotation shafts 171 and 172, and the leaf plate 141m is constantly tensioned in a closing direction of the irradiation field by the driving gear 150 foxed to either one drum of the constant force spring 160.

As illustrated in FIG. 6, a right-side edge surface of the leaf plate 141m is connected to a wire 151. The wire 151 may be a piano wire. The wire 151 is rolled up by an axis of a motor 153 through at least one pulley 152. When the wire 151 is rolled up by rotations of the motor 153, the leaf plate 141m is moved in an opening direction (the right direction of the drawing) while a force is constantly applied to the leaf plate 141m in the closing direction by the driving gear 150 coaxially connected to the constant force spring 160.

Thus, the leaf plate 141m is moved in the opening direction so as to position of a desired irradiation field by rolling up the wire 151 through the motor. When the leaf plate 141m is moved in the opening direction, the driving gear 150 connected to the constant force spring 160 applies a constant force to the leaf plate 141m in the closing direction by engaging with the toothed configuration of the leaf plate 141m. By doing so, backlashes due to engagement with the driving gear 150 are substantially eliminated.

The moving amount of the leaf plate 141m in the opening direction is controlled by a roll-up amount of the motor 153. Thus, the control section 30 (FIG. 1) controls the roll-up operation of the motor 153 so as to set up the irradiation field U of the leaf plate 141m at a position in accordance with the shape T of the target treatment region.

Figure 11:
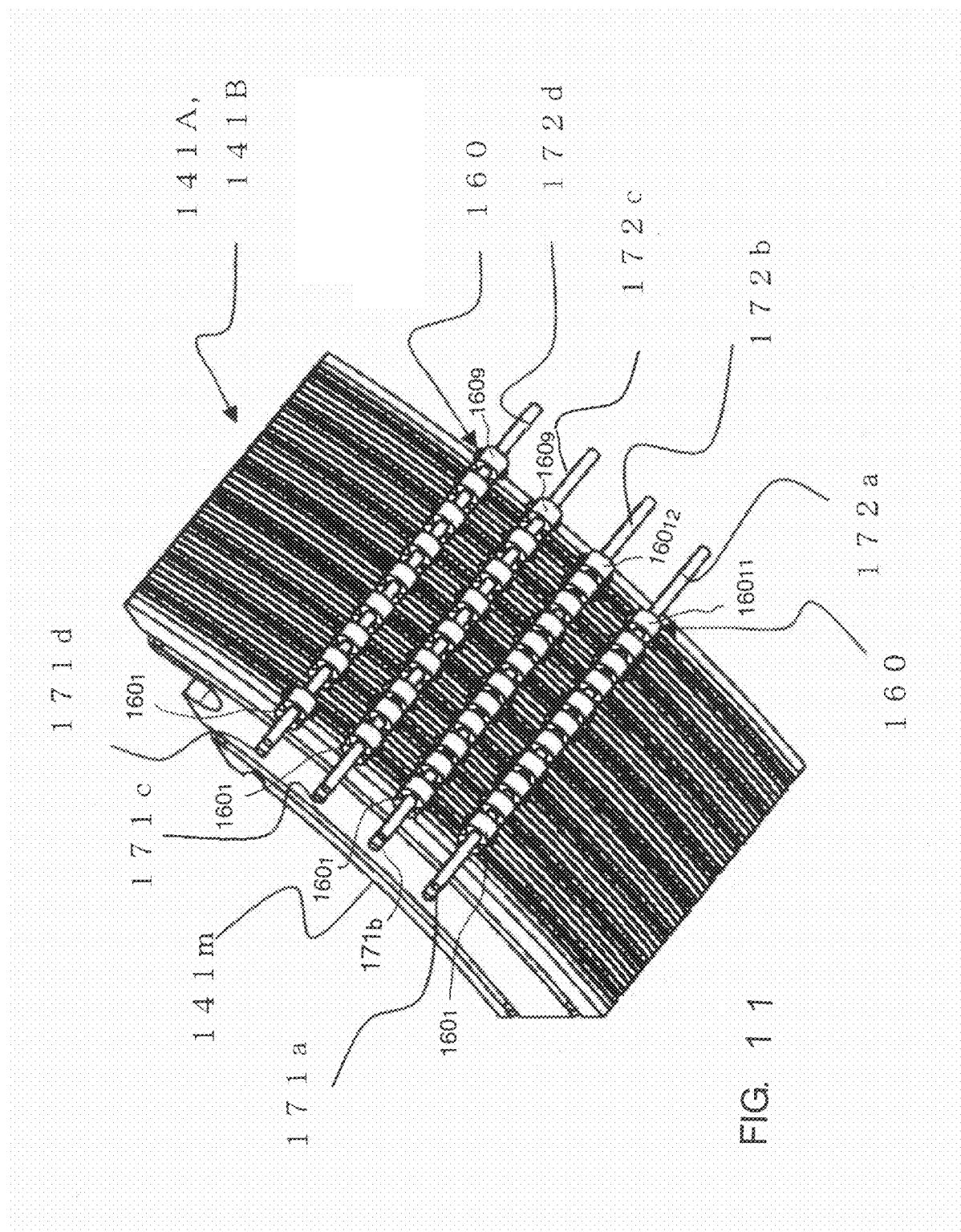
FIG. 11 is a lower appearance the leaf plates driving mechanism illustrated in FIG. 10.

As illustrated in FIG. 4, each of the pair of lower collimator blocks 141A and 141B is respectively constructed by a plurality of leaf plates 141A1 through 141An and 141B1 through 141Bn. To independently move all of the leaf plates in the lower collimator block, a plurality of pairs of rotation shafts is provided along the moving direction of the lower collimator blocks for supporting the same number of driving mechanisms to the plurality of constant force springs 160. Each pair of rotation shafts respectively supports a different plural number of constant force springs in the X direction. Thus, in this embodiment, four (4) pairs of rotation shafts are provided in the Y direction, where a first pair of rotation shaft supports eleven (11) constant force springs, a second pair of rotation shaft supports twelve (12) constant force springs, and third and fourth pairs of rotation shafts respectively support nine (9) constant force springs as illustrated in FIG. 11.

Figure 9:
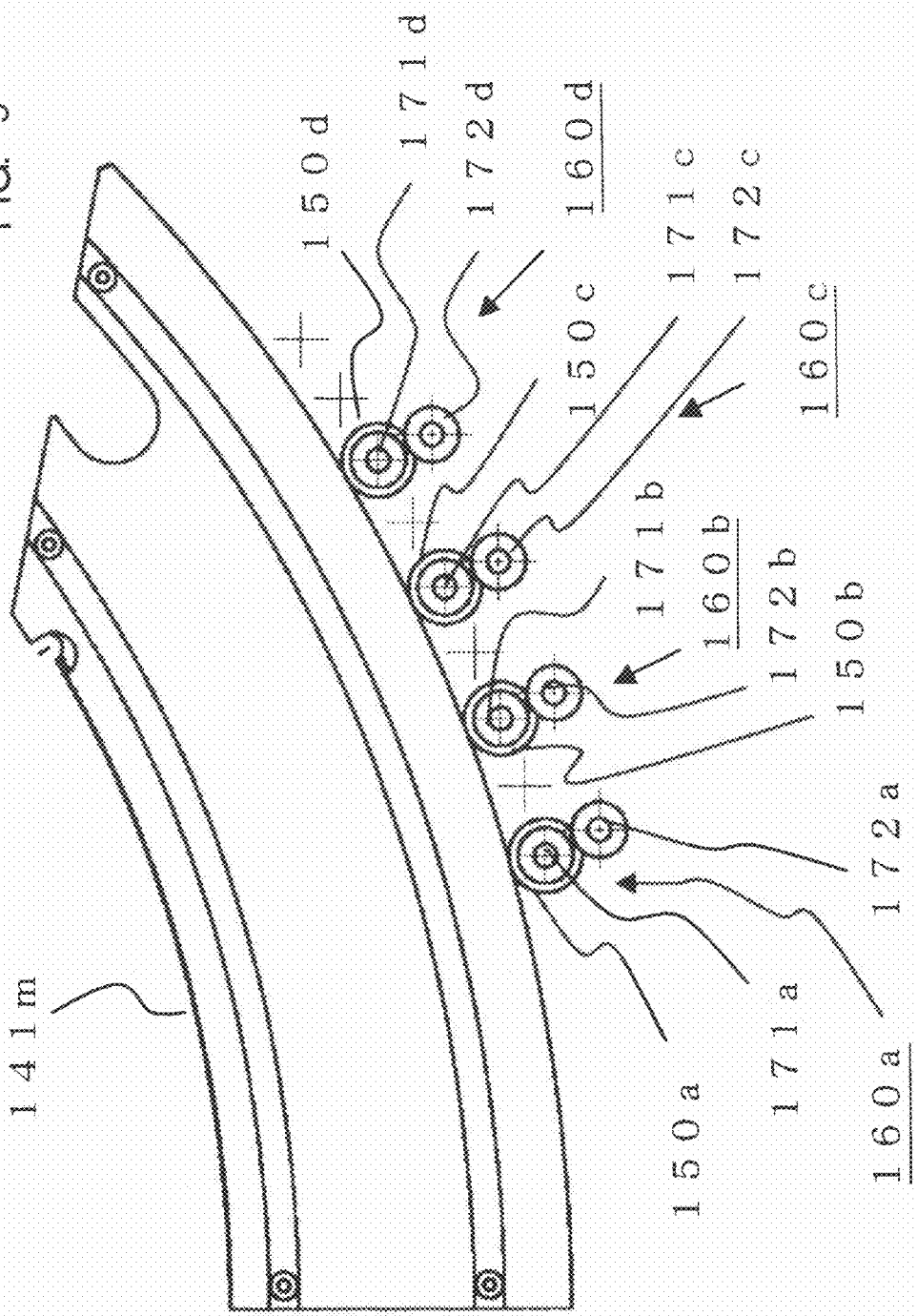
FIG. 9 illustrates a leaf plate drive mechanism using a plurality of constant force springs.

FIG. 9 is a side view of an example of driving mechanism of the either one of the lower collimator blocks. In the embodiment, four pairs of rotation shafts are provided for driving each of leaf plate 141m. For instance, one of a plurality of driving gears 150a fixed on one of a plurality of constant force springs 160a that is supported on a first pair of rotation shafts 171a and 172a is engaged with a first leaf plate $141_1$, and another one of the plurality of driving gears supported by the same first pair of rotation shafts 171a and 172a is engaged, for example, with each toothed configuration of a fifth leaf plate 1415 and a tenth leaf plate $141_{10}$ (either not shown). Similarly, the driving gears 150b of a plurality of constant force spring 160b supported by the second pair of rotation shafts 171b and 172b engaged with the toothed configuration of the second leaf plate $141_2$, and another driving gears supported by the second rotation shafts are engaged with the toothed configurations of, for instance, the sixth leaf plate $141_6$ and the eleventh leaf plate $141_{11}$. Similarly, the driving gears 150c of the plurality of constant force spring 160c supported by the third pair of rotation shafts 171c and 172c engage with the toothed configurations of the third leaf plate $141_3$, the seventh leaf plate $141_7$ and the twelfth leaf plate $141_{12}$. The driving gears 150d of the plurality of constant force spring 160d supported by the fourth pair rotation shafts 171d and 172d engage with the toothed configurations of the fourth leaf plate $141_4$, the eighth leaf plate $141_8$ and the thirteenth leaf plate $141_{13}$.

By such a construction, a large number of driving gears can respectively engage with the large number of constant force springs by supporting the large number of constant force springs with a small number of rotation shaft pairs arranged along a tracking surface direction (X direction) of the lower irradiation collimator block. Consequently, it becomes possible to independently move an increased large number of leaf plates 141m in a limited space of the irradiation unit 13.

Figure 10:
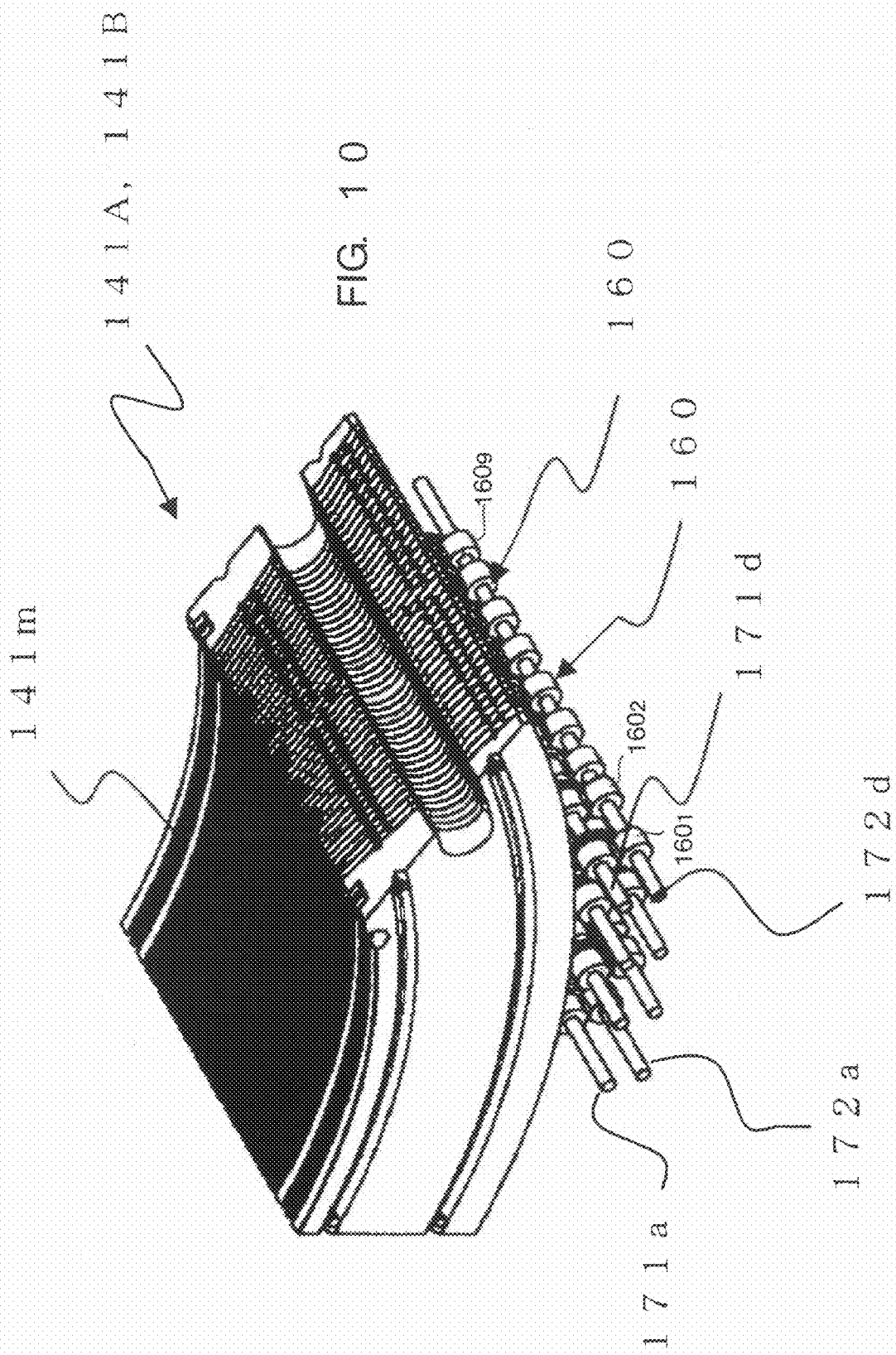
FIG. 10 is a perspective view of leaf driving mechanism leaf plates driving mechanisms illustrating each of a plurality of leaf plates is engaged to each driving gears connected to a respective constant force spring.

FIG. 10 is a perspective view of the leaf plate driving mechanism in FIG. 9. FIG. 11 is an under perspective view of the leaf plate driving mechanism in FIG. 10. Only one block of the lower collimator blocks 141A and 141B is depicted in FIGS. 10 and 11. In the present embodiment, different number of constant force springs is respectively supported on each of four pairs of rotation shafts 171a and 172a through 171d and 172d. For instance, each of the driving gears $150_1$, $150_2$, ---, $150_{11}$ fixed to a plurality of constant force springs $160_1$, $160_2$, ---, $160_{11}$ supported by the first pair of rotation shafts 171a and 172a is engaged with the toothed configurations provided on each of the leaf plates $141_1$, $141_2$, ---, $141_{11}$ for driving each of the leaf plates. In the embodiment, eleven of constant force springs $160_1$, $160_2$, ---, $160_{11}$ are supported by the second pair of rotation shafts 171b and 172b along the X direction. the third pair of rotation shafts 171c and 172c and on the fourth pair of rotation shafts 171d and 172d, nine of the constant force springs $160_1$, $160_2$, ---, $160_9$ are supported in the X direction. Thus, by supporting an appropriate number of constant force springs 160 on one pair of rotation shafts and also by arranging the plural number of constant force springs supported on different pairs of rotation shaft in staggered position with each other in the X direction, it becomes possible to install an increased number of leaf plates 141m in a limited space of the irradiation head unit.

Figure 12:
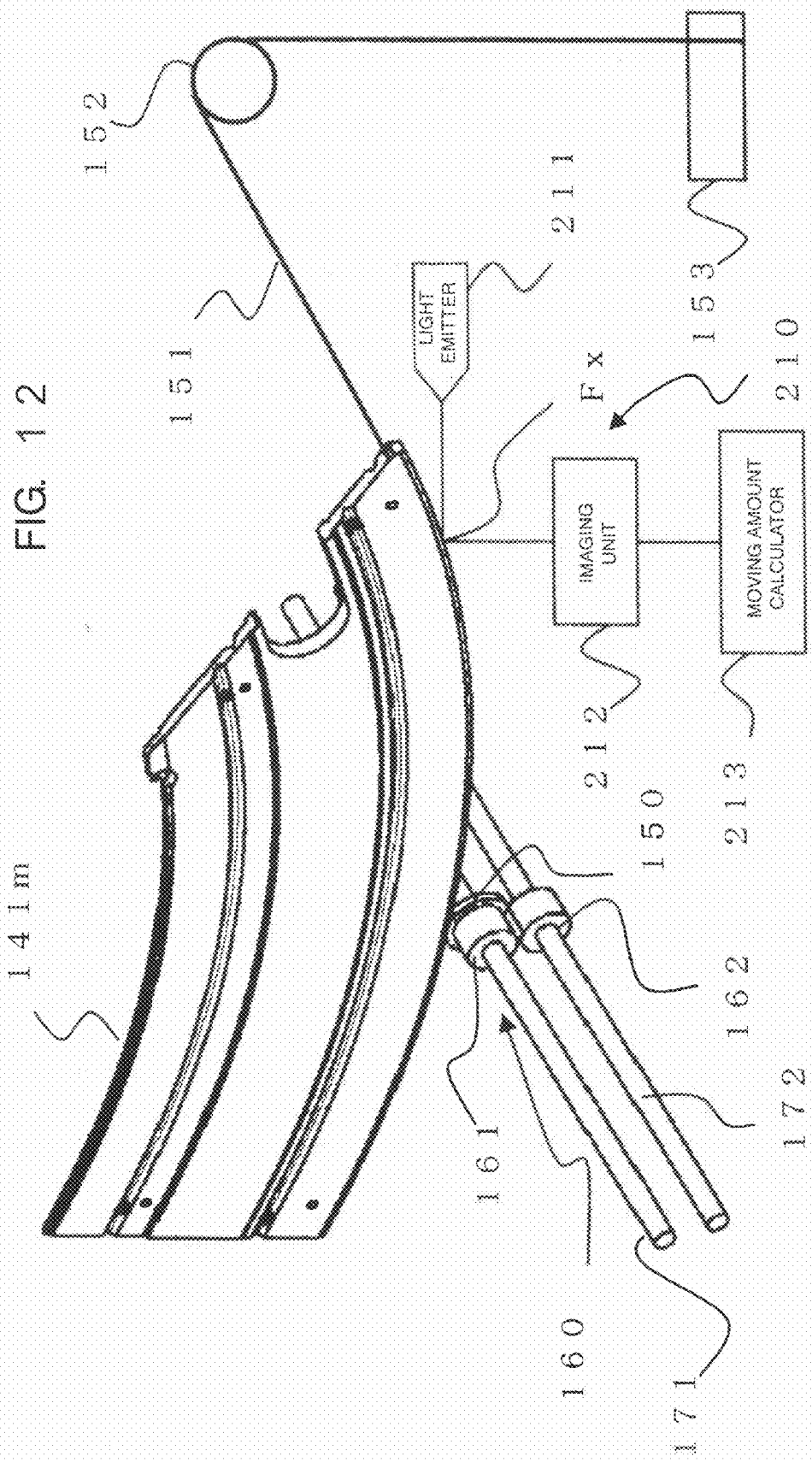
FIG. 12 is a block diagram illustrating an embodiment of a leaf plate position detector.
Figure 13:
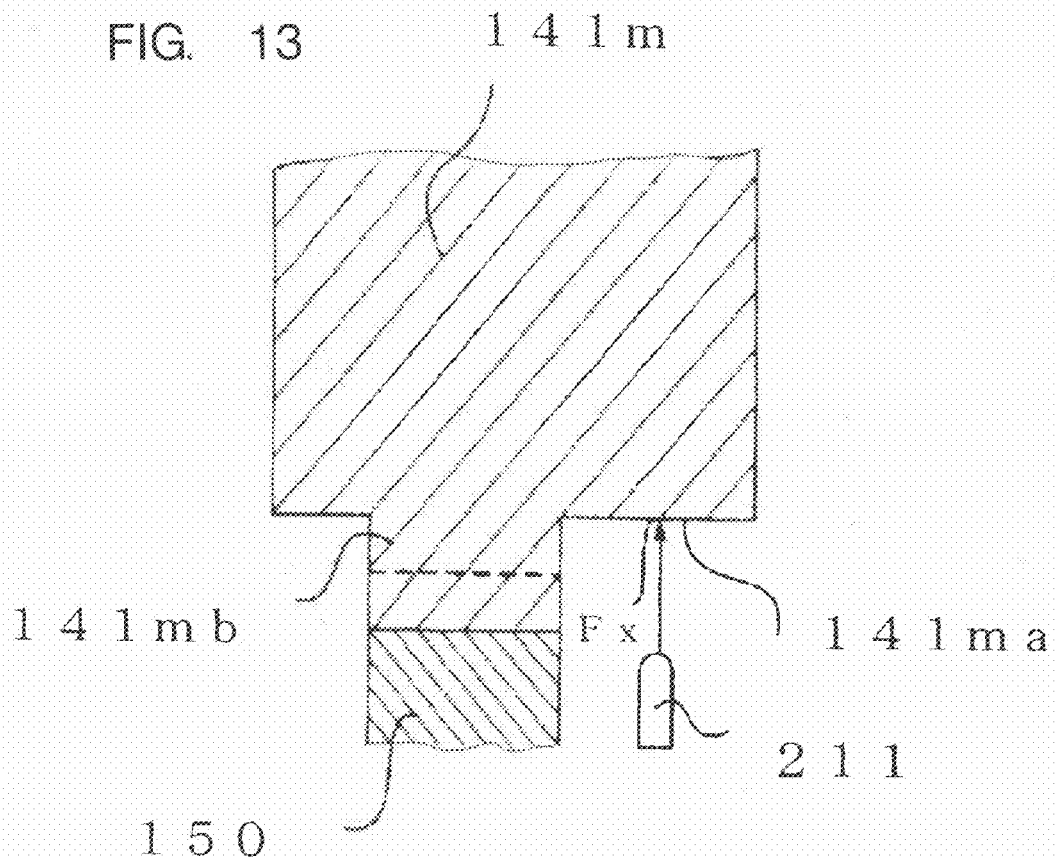
FIG. 13 is a cross-sectional view of an outer edge surface of a leaf plate according to the embodiment.
Figure 14:
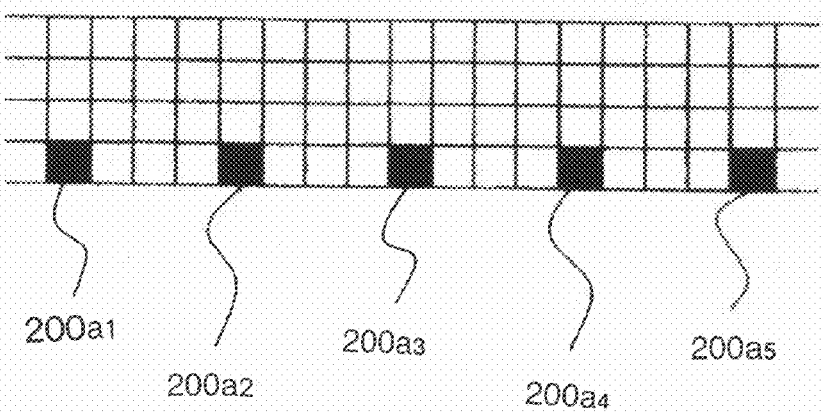
FIG. 14 is an exemplary pattern formed on an outer edge surface of the leaf plate illustrated in FIG. 13.

The opening and closing operations of the leaf plate 141m for forming an irradiation field U as approximately to a configuration T of the target treatment region (FIG. 5) are performed by rolling up each wire through each motor 153 under controlling of the control section 30. FIG. 12 illustrates a construction of the position detection unit 210 for a leaf plate 141m. FIG. 13 illustrates a partial section view of an outer edge portion 141ma of the leaf plate 141m. The toothed configuration 141mb (not shown) is formed on an arc shaped outer edge surface 141ma of a leaf plate 141m. A driving gear 150 fixed to the first drum 161 of each constant force spring 160 is engaged with the toothed configuration 141mb. As illustrated in FIG. 13, the outer edge surface 141ma of the leaf plate includes a toothed configuration portion 141mb and a non-toothed configuration portion 141mb in a width direction of the plate. On the non-toothed configuration portion 141mb, a light reflecting pattern 200 is fixed along the moving direction (Y direction) of the leaf plate 141m. FIG. 14 is an exemplary light reflecting pattern 200.

As illustrated in FIG. 12, a light is emitted from a light emitting unit 211 to a fixed point Fx of the pattern 200 fixed on the outer edge surface 141ma of the leaf plate 141m. An imaging unit 212 provided near the leaf plate 141m acquires an image of the fixed point by imaging over a region including the fixed point Fx on the pattern 200. The light emitting unit 211 may be constructed by, for instance, light emitting diodes. The imaging unit 212 may be constructed by, for instance, a CCD camera. Output signal from the imaging unit 212 is supplied to a moving amount calculation unit 213. The moving amount calculation unit 213 may be provided in the control section 30.

FIG. 14 is an exemplary light reflecting pattern 200. The pattern 200 is, as an example, a square region of 0.5 mm in four directions is divided into sixteen small squares in a net-like structure. By blacking out each corner of the small squares, special patterns $200a_1$ through $200a_5$ are formed. The special pattern is, of course, formed in other techniques than the coloring.

The light emitting unit 211 emits a light for irradiating a portion of the pattern 200 including the fixed point Fx. The fixed point Fx is located at a position that is not influenced by a displacement of the leaf plate 141m, and has a certain area. A setting position and an emitting direction of the light emitting unit 211 are fixed so as to set up the fixed point Fx along an arc direction of the outer side of the leaf plate 141m and to include a part region of the pattern 200.

An imaging unit 212 is provided so as to image a region including the fixed point Fx on the pattern 200. Thus, the imaging unit 212 acquires the images of fixed points at a prescribed interval by time sequentially receiving reflected lights from the fixed point Fx. In the images of fixed points, the pattern 200 provided on the leaf plate 141m partially exists. The moving amount calculation unit 213 specifies a position of a special pattern 200a included in the pattern 200 and calculates a moving amount of the leaf plate 141m based on time sequential displacements of the special pattern 200a acquired through the imaging unit 212.

The moving amount calculation unit 213 analyses images of a plurality of fixed points acquired in a time sequence in accordance with movements of the leaf plate 141m and acquires a moving amount of the leaf plate 141m. Since the pattern 200 fixed on the leaf plate 141m in accompany with the movement of the leaf plate 141m, each position of the fixed point Fx on the pattern 200 relatively changes in the plurality of fixed point images. Thus, by judging the position displacements of the fixed point Fx on the plurality of fixed point images time sequentially acquired through the moving amount calculation unit 213, the leaf plate position detection unit 210 can detect a moving amount of the leaf plate 141m.

Despite of displacement amount of the leaf plate 141m, a part of or the whole of the special pattern 200a is desired to exist in the image of the fixed point. Thus, the pattern 200 formed on the leaf plate 141m is desirable to be a small as possible. In the present embodiment, the special pattern 200a is formed by a square of 0.5 mm in four directions as one unit of the pattern 200 for making a smaller area than an imaging area of the imaging unit 212.

According to the radiation therapy equipment in consistent with the present embodiment, since each leaf plate is constantly tensioned in both a closing direction and an opening direction, an irradiation field can be accurately set up with substantially avoiding backlashes due to the driving gears. According, unnecessary irradiation of radiation on normal tissues can be protected. Even when a wire for tensioning a leaf plate in an opening direction is cut, the leaf plate moves in a closing direction by the force of the constant force spring to protect an object from unnecessary irradiation. Thus, a safety of the patient can be constantly protected.

In the present embodiment, since a plurality of constant force springs is fixed on a pair of rotation shafts for driving the same number of the constant force springs, it becomes possible to reduce the numbers of the shafts for rotating the leaf plate driving gears comparing to the conventional radiation therapy equipment. Further, since each wire connected to each leaf plate can change direction through pulleys, it becomes possible to freely place a plurality of roll-up motors at appropriate positions in a limited space. Thus, an increased number of roll-up motors can be installed in a limited space of the irradiation unit. Consequently, it becomes possible to increase the number of leaf plates can so as to set up the irradiation field in a higher accuracy.

According to the present embodiment, since a displacement and a position of a leaf plate can be detected by a non-contact system, displacements or detection errors of plate positions due to backlashes and wearing of toothed wheels are eliminated. Consequently, each position of a leaf plate can be accurately detected, and each irradiation field can be set up in a high accuracy.

In place of the motor used in the embodiment, it is also possible to roll up the wire connected to the leaf plate by using powers of hydraulic pressure or air pressure. While a position of the leaf plate is directly detected by the leaf plate position detection unit in the embodiment, it is also possible to detect the leaf plate position by a non-contact detection system. For instance, a multi-pole magnetic pattern is attached on a side surface of a driving gear. And a magnetic sensor provided near the driving gear detects the magnetic pattern. Based on detected data through the magnetic sensor, each moving amount of a leaf plate can be controlled.

While certain embodiments have been described, these embodiments are presented by way of example only, and are not intended to limit the scope of the invention. Indeed, the novel instruments described herein may be embodied in a variety of other forms; furthermore, various omissions and changes in the form of the instruments described herein may be made without departing from the spirit of the inventions. The accompanying claims and their equivalents are intended to cover such forms or modifications as would fall within the scope and spirit of the inventions.

The invention claimed is:

1. Radiation therapy equipment including a radiation collimator unit for setting a desired irradiation field onto a target treating region by shielding radiation on unnecessary regions, the radiation therapy equipment comprising:
    a pair of movable collimator blocks, each block including a plurality of movable leaf plates, each leaf plate having a toothed configuration on an arc shaped tracking surface on the leaf plate;
    a plurality of driving gears configured to independently drive each of the plurality of leaf plates by engaging with the toothed configuration provided on each tracking surface of the plurality of leaf plates;
    a plurality of constant force spring units coupled to each of the plurality of driving gears configured to constantly apply a direct force to each of the plurality of driving gears so as to independently move each of the plurality of leaf plates in closing directions;
    a plurality of wires connected to each of the plurality of leaf plates; and
    a plurality of roll-up units configured to independently roll-up each of the plurality of wires so as to independently move each of the leaf plates in an opening direction against each of the closing forces of the plurality of constant force spring units.

2. In the radiation therapy equipment according to claim 1, wherein the radiation collimator unit comprises:
    a pair of upper collimator blocks provided at a near position of the radiation source, each block having a first toothed configuration on a first arc shaped tracking surface so as to move along a first moving track;
    a pair of driving gear units configured to drive the pair of upper collimator blocks by engaging with the toothed configurations provided on each of the tracking surfaces;
    a pair of lower collimator blocks provided under the pair of upper collimator blocks, each block being formed with a plurality of leaf plates, and each plate having a second toothed configuration on a second arc shaped tracking surface so as to orthogonally move crossing the first moving track;
    wherein each of the lower collimator blocks comprises:

a plurality of driving gears configured to independently move each of the plurality of leaf plates engaging with the second toothed configuration;

a plurality of constant force spring units coupled to each of the plurality of driving gears so as to independently apply a constant force in a closing direction;

a plurality of wires connected to the plurality of leaf plates; and a plurality of roll-up units configured to independently roll-up the plurality of wires so as to independently move each of the plurality of leaf plates in an opening direction against the force applied by the plurality of constant force spring units.

3. The radiation therapy equipment according to claim 2, wherein each of the plurality of constant force spring units is comprised of two drums for winding up a plate spring, and each of the plurality of constant force spring units is supported by a pair of rotation shafts; and each shaft penetrates each of center apertures of the two drums.

4. The radiation therapy equipment according to claim 3, wherein the plurality of constant force springs is supported by a plurality of pairs of rotation shafts arranged in a direction of the first arc shaped track.

5. The radiation therapy equipment according to claim 4, wherein first ones of the plurality of driving gears are coaxially supported on one pair of rotation shafts and second ones of the plurality of driving gears are coaxially supported on another pair of rotation shafts, and the first and second ones of the plurality of driving gears are arranged in staggered positions.

6. The radiation therapy equipment according to claim 3, wherein each of the plurality of driving gears engaged to each toothed configuration of the plurality of leaf plates is connected to one of the two drums forming the constant force spring.

7. The radiation therapy equipment according to claim 6, further comprising a control unit configured to independently control a moving amount of each of the leaf plates in the opening direction by each of the plurality of roll-up units so as to set an irradiation field of radiation in accordance with a position of each of the leaf plates and a target shape of a treatment region.

8. The radiation therapy equipment according to claim 1, wherein the plurality of leaf plates is respectively attached to a plurality of wires, and the plurality of roll-up units independently roll-up the plurality of wires so as to move each of the leaf plates in an opening direction against the force of the spring unit in a closing direction.

9. The radiation therapy equipment according to claim 1, wherein each of the plurality of roll-up units includes a motor for winding up the wire so as to move the each of the leaf plates at a desired position in order to form the irradiation field.

10. The radiation therapy equipment according to claim 9, wherein each of the plurality of roll-up units winds up the wire to a corresponding one of the motors through a pulley and the plurality of roll-up units is freely installed in a space in the radiation collimator unit.

11. The radiation therapy equipment according to claim 1, further comprising a detection unit configured to detect a position or a moving amount of each of the leaf plates by a non-contacted detection of a specific pattern fixed on a tracking surface of each of the leaf plates.

12. The radiation therapy equipment according to claim 1, further comprising a magnetic sensor provided near the driving gears for acquiring detection data on a multi-pole magnetic pattern attached on a peripheral surface of the driving gear; and a moving amount of each of the plurality of leaf plates is controlled based on the detection data.

13. A radiation therapy equipment comprising:

a radiation source;

an upper irradiation collimator unit provided near the radiation source along an irradiation axis of the radiation source; and a lower irradiation collimator unit provided under the upper irradiation collimator unit along the irradiation axis so as to orthogonally cross a moving direction of the upper irradiation collimator unit; the upper irradiation collimator unit and the lower irradiation collimator unit are moved so as to determine an irradiation aperture for irradiating an object;

wherein the lower irradiation collimator unit is comprised of:

a plurality of movable leaf plates, each having a toothed configuration on one curved edge of the leaf plate;

a plurality of driving gears for respectively engaging to each of the toothed configurations of the plurality of movable leaf plates;

a plurality of spring units coupled to each of the plurality of driving gears for respectively applying a direct force to each of the plurality of movable leaf plates through each of the plurality of the driving gears so as to independently move in a closing direction of the irradiation aperture;

a plurality of wires connected to each of the plurality of movable leaf plates; and a plurality of wire drive units configured to drive each of the plurality of wires so as to move in an opening direction of the irradiation aperture.

* * * * *